United States Patent [19]

Wehrli

[11] 3,953,518
[45] Apr. 27, 1976

[54] PROCESS FOR PREPARING γ, δ-UNSATURATED CARBONYL COMPOUNDS

[75] Inventor: Pius Anton Wehrli, North Caldwell, N.J.

[73] Assignee: Hoffmann-La Roche Inc., Nutley, N.J.

[22] Filed: Dec. 23, 1974

[21] Appl. No.: 535,591

Related U.S. Application Data

[63] Continuation-in-part of Ser. No. 376,500, July 5, 1973, abandoned.

[52] U.S. Cl. .................. 260/593 R; 260/476 R; 260/586 R; 260/594; 260/598; 260/599; 260/601 R; 260/602
[51] Int. Cl.² .................................. C07C 45/00
[58] Field of Search ........ 260/593 R, 476 R, 586 R, 260/601

[56] References Cited
UNITED STATES PATENTS

3,453,317   1/1969   Marbet et al. ............... 260/593 R

OTHER PUBLICATIONS

Migidichian I, "Organic Synthesis", Vol. I, p. 194 (1957).

Laitinen, Chemical Analysis, pp. 43–46, and 60–61 (1960).

Migidichian II, "Organic Synthesis", Vol. I, pp. 862 (1957).

*Primary Examiner*—James O. Thomas, Jr.
*Assistant Examiner*—James H. Reamer
*Attorney, Agent, or Firm*—Samuel L. Welt; Bernard S. Leon; Richard A. Gaither

[57]   ABSTRACT

γ, δ-Unsaturated carbonyl compounds are prepared by reacting a tertiary allyl alcohol with an acetal or ketal of an aliphatic aldehyde or ketone in the presence of an acid catalyst system consisting of a strong acid and a weak acid.

4 Claims, No Drawings

PROCESS FOR PREPARING γ,δ-UNSATURATED CARBONYL COMPOUNDS

CROSS-REFERENCE TO RELATED APPLICATIONS

This application is a continuation-in-part of United States Patent Application Ser. No. 376,500 filed July 5,1973 now abandoned.

BACKGROUND OF THE INVENTION

This invention relates to an improved process for obtaining γ,δ-unsaturated carbonyl compounds by the reaction of a tertiary allyl alcohol with an acetal or ketal of an aliphatic aldehyde or ketone in the presence of an acid catalyst.

Heretofore, unsaturated carbonyl compounds have been prepared by using, as the acid catalyst, a strong acid, such as a mineral acid, a strong organic acid or a strong acid salt. See U.S. Pat. No. 3,453,317. The yields from such processes using a strong acid catalyst have been found, however, to be relatively low. For example, in Example 3 of the aforementioned patent, the reaction of the tertiary allyl alcohol, 3-methyl-1-buten-3-ol, with the ketal, acetone dimethyl ketal, in the presence of phosphoric acid provided yields of the γ,δ-unsaturated ketone, 6-methyl-5-hepten-2-one, of only 54%.

SUMMARY OF THE INVENTION

IN accordance with this invention, a process is provided for obtaining γ,δ-unsaturated carbonyl compounds of the formula:

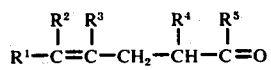

$$R^1-C=C-CH_2-CH-C=O \quad \text{I}$$
(with $R^2, R^3$ above first $C=C$ and $R^4, R^5$ above $CH-C$)

wherein $R^1$ is selected from the group consisting of (a) a saturated hydrocarbon group, (b) an unsaturated hydrocarbon group, (c) an aralkyl group, (d) an aryl group, and (e) an oxygencontaining derivative of (a), (b), and (c) wherein the oxygen is in the form of free hydroxy, esterified hydroxy, wherein the esterifying group is an acyloxy group in which the acyl moiety is from an acid selected from the group consisting of lower alkanoic acids and benzoic acid, and etherified hydroxy selected from the group consisting of lower alkoxy and phenyloxy, and wherein the oxygen atom is attached to an aliphatic carbon atom on said group; $R^2$ is a lower aliphatic hydrocarbon; $R^3$, $R^4$, and $R^5$ are selected from the group consisting of hydrogen and lower aliphatic hydrocarbon; and wherein $R^1$ taken together with $R^2$ can form a carbocyclic ring, and
$R^4$ taken together with $R^5$ can form a carbocyclic ring;
by reacting a tertiary allyl alcohol of the formula:

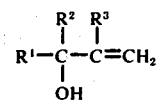

wherein $R^1$, $R^2$ and $R^3$ are as above;

with an acetal or ketal of the formula:

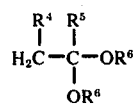

wherein $R^4$ and $R^5$ are as above and $R^6$ is alkyl;
in the presence of an acid catalyst system consisting of a strong acid and a weak acid.

In accordance with this invention the reaction is carried out by incrementally adding the tertiary alcohol of formula II to the reaction medium containing the acetal or ketal of formula III and the acid catalyst system consisting of the strong acid and the weak acid to provide 3 to 100 moles of the acetal of formula III and 1 mole of the alcohol of formula I. The reaction is carried out by reacting each increment of the tertiary alcohol of formula II with the compound of formula III to form the compound of formula I and an alcohol of the formula $$R^6-OH \quad \text{IV}$$

wherein $R^6$ is as above. The alcohol of formula IV forms an azeotrope with the acetal of formula III which is distilled off the reaction mixture prior to the addition of the next increment of tertiary alcohol added to the reaction mixture.

By this process γ,δ-unsaturated carbonyl compounds can be obtained in yields of about 80% or more with approximately complete consumption of the tertiary allyl alcohol.

DETAILED DESCRIPTION OF THE INVENTION

In accordance with this invention, a γ,δ-unsaturated carbonyl compound of formula I is obtained by reacting a tertiary allyl alcohol of formula II with an acetal or ketal of formula III in the presence of an acid catalyst system consisting of at least one strong acid and at least one weak acid.

The compounds of formula I preparable according to the process of this invention include compounds wherein $R^1$ is a straight chain, branched chain or cyclic aliphatic hydrocarbon group. Among the preferred hydrocarbon groups represented by $R^1$ are the following saturated and unsaturated hydrocarbon groups: lower alkyl and lower alkenyl groups, e.g., methyl ethyl, propyl, isopropyl, butyl, isobutyl, 3,4-dimethylpentyl, vinyl, allyl, 3,4-dimethylpenten-3-yl; higher alkyl and higher alkenyl groups, e.g., a group of the formula:

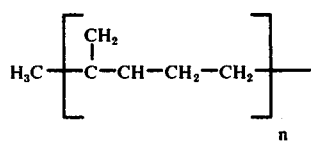

wherein $n$ is a whole number from 1-8, inclusive, and the bond illustrated dotwise can also be hydrogenated;
4,7,8,-trimethyl-nonyl, 4,7,8,-trimethyl-nonadien-3,7-yl, etc., as well as lower and higher alkyl and alkenyl groups such as the above. The especially preferred hydrocarbon groups encompassed by $R^1$ are the straight chain and branched chain lower alkyl groups, having 1 to 7 carbon atoms, particularly methyl.

Also among the compounds of formula I preparable according to the process of this invention are compounds wherein $R^1$ is an aralkyl group, preferably a phenyl lower alkyl group, or an aryl group, preferably a phenyl group. Further among the unsaturated carbonyl compounds of this application are included compounds wherein $R^1$ is a lower or higher alkyl or alkenyl group or an aralkyl group, such as above, carrying an oxygen-containing substituent attached to an aliphatic carbon atom, specifically a free, esterified, or etherified hydroxy group. Esterified hydroxy groups include acyloxy groups in which the acyl group is from a lower alkanoic acid or an arloweralkanoic acid such as formic acid, acetic acid, propionic acid, butyric acid, etc., or benzoic acid. Etherified hydroxy groups are preferably lower alkoxy groups, e.g., methoxy, propoxy, isopropoxy, etc., or aryloxy groups such as phenyloxy, etc. Specific examples of oxygen-containing $R^1$ groups includes hydroxymethyl, acetoxyethyl, methoxypropyl, 4-hydroxy (or methoxy or acetoxy)-4-methylpentyl, 8-hydroxy (or methoxy or acetoxy)-4,8-dimethylnonyl, 8-hydroxy (or methoxy or acetoxy)-4,8-dimethyl-nonen-3-yl,4-hydroxy (or methoxy or acetoxy)-3,4-dimethyl-pentyl, etc. When the $R^1$ group contains an oxygen-containing substituent, the elements making up the $R^1$ group are only carbon, hydrogen, and one oxygen atom. When the $R^1$ group does not contain an oxygen-containing substituent, the elements making up the $R^1$ group are carbon and hydrogen only.

The $\gamma,\delta$-unsaturated carbonyl compounds of formula I preparable according to this application also include compounds wherein $R^2$, $R^3$, $R^4$ and $R^5$ are straight chain, branched chain or cyclic lower aliphatic hydrocarbon groups. Among the preferred lower aliphatic hydrocarbon groups represented by $R^2$, $R^3$, $R^4$ and $R^5$ are the lower alkyl and lower alkenyl groups having from 1 to 8 carbon atoms, e.g., methyl, ethyl, propyl, isopropyl, allyl, butyl, pentenyl, etc. The particularly preferred lower aliphatic hydrocarbon groups is methyl. $R_3$ is preferably hydrogen.

The unsaturated carbonyl compounds preparable according to this application further include compounds wherein $R^1$ and $R^2$ taken together and $R^4$ and $R^5$ taken together can form rings. Among such rings are the carbocyclic 5- and 6-membered rings containing only the elements carbon and hydrogen, such as $R^1$ together with $R^2$ forming a tetramethylene or pentamethylene group and $R^4$ together with $R^5$ forming a trimethylene or tetramethylene group.

In forming the $\gamma,\delta$-unsaturated carbonyl compounds of formula I, $R_6$ is a straight chain or branched chain alkyl group of 1 to 20 carbon atoms. Preferably, $R_6$ is a lower alkyl group of from 1 to 8 carbon atoms, particularly methyl or ethyl.

Among the tertiary alcohols of formula II which can be utilized in the process of this invention are included:
3-methyl-1-buten-3-ol;
2,3-dimethyl-1-buten-3-ol;
3-methyl-1-penten-3,5-diol;
3-methyl-1-penten-3-ol;
3,5-dimethyl-1-hexen-3-ol;
3-phenyl-1-buten-3-ol;
3-phenyl-1-buten-3-ol;
1-vinyl-1-cyclohexanol;
1-vinyl-1-cyclopentanol;
3,7-dimethyl-1,6-octadien-3-ol (linalool);
3,7-dimethyl-1-octen-3,7-diol;
3,6,7-trimethyl-1,6-octadien-3-ol;
3,7-dimethyl-1-octen-3-ol;
3,6,7-trimethyl-1-octen-3-ol;
3,6,7-trimethyl-7-ethoxy-1-octen-3-ol;
3,7,11-trimethyl-1,6,10-dodecatrien-3-ol (nerolidol);
3,7,11-trimethyl-1-dodecaen-3-ol (tetrahydronerolidol); isophytol; and
3,7-dimethyl-7-methoxy-1-octen-3-ol (methoxylinalool).

Among the ketals and acetals of formula III which can be utilized in forming the $\gamma,\delta$-unsaturated carbonyl compounds of formula I in accordance with this application are included: acetone dimethyl ketal; acetone diethyl ketal; 2,2-dimethoxybutane; 2,2-diethoxy pentane; 3,3-dimethoxy-pentane; 4-methyl-2,2-diethoxy-pentane; 1,1-dimethoxy-cyclohexane; acetaldehyde diethyl acetal; propionaldehyde dimethyl acetal; butyraldehyde diethyl acetal; enanthaldehyde diethyl acetal; etc.

In the process of this application, any conventional strong acid having a pK value (the negative logarithm of the dissociation constant) from about 0.4 to about 3 can be utilized in the acid catalyst system. Preferably, an acid having a pK value of about 2 is utilized in the acid catalyst system. Among the strong acids which can be utilized are: the mineral acids, such as phosphoric acid, sulfuric acid and hydrochloric acid; and the strong organic acids, such as oxalic acid, trichloroacetic acid, trifluoroacetic acid, and the sulfonic acids, such as the toluene sulfonic acids, particularly paratoluene sulfonic acid, the lower alkyl sulfonic acids, particularly methyl sulfonic acid, and the nitrophenyl sulfonic acids. Also among the strong acids which can be utilized are the strong acid salts, such as potassium bisulfite, boron trichloride, zinc chloride, boron chloride and ferric chloride. The preferred strong acid is phosphoric acid.

In the process of this application, any conventional weak acid having a pK value of from about 4 to about 10 can be utilized in the acid catalyst system. Preferably an acid having a pK value of about 4.5 to 6, especially an acid having a pK value of about 5, is utilized in the acid catalyst system. Among the weak acids which can be utilized in this process are included: the lower alkanoic acids such as formic, acetic and pivalic acids; the dinitro benzoic acids, such as 2,4-dinitro benzoic acid; and dinitrophenol. The preferred weak acid is acetic acid.

The tertiary allyl alcohol of formula II can be reacted with the ketal or acetal of formula III to form the $\gamma,\delta$-unsaturated carbonyl compound of formula I, in accordance with the process of this invention, by heating the reactants above about 50°C. in the presence of the acid catalyst system consisting of a strong acid and a weak acid. In carrying out this reaction, the particular elevated temperature and pressure utilized are not critical, and the reaction can be suitably carried out at temperatures from 100°C. up to about 200°C. at a pressure at or above the vapor pressure of the reaction mixture. Preferably, the reaction is carried out at a pressure of 10 to 50 atmospheres and within a temperature range of about 120° to about 180°C., particularly at about 150°C.

The reaction can if desired by carried out in a solvent medium. As a solvent there can be used any conventional, inert organic solvent. The preferred solvents are the aromatic and aliphatic hydrocarbons, such as hexane, cyclohexane, isooctane, benzene, toluene, petroleum ether and ligroin.

In carrying out the process of this application, an excess of the ketal or acetal of formula III is utilized, particularly a molar ratio of ketal or acetal of formula III to allyl alcohol of formula II of approximately 3:1. The amount of the acid catalyst system utilized in the reaction is also not critical, and the catalyst system can suitably comprise between about 0.1% by weight and 10% by weight of the reaction mixture. Preferably, the catalyst system comprises about 1% by weight of the reaction mixture.

The ratio of strong acid to weak acid in the acid catalyst system is also not critical. Preferably, the strong acid comprises from about 2 to about 15% by weight of the acid catalyst system, with the weak acid comprising between about 85 to 98% by weight of the acid catalyst system. It is particularly preferred that the strong acid comprise about 5 to 10% by weight of the acid catalyst system and that the weak acid comprise about 90 to 95% by weight of the catalyst system. In this catalyst system, the strong and the weak acid may themselves be mixtures of acids.

In accordance with a second embodiment of this invention, a $\gamma,\delta$-unsaturated carbonyl compound of formula I is obtained by reacting a tertiary allyl alcohol of formula II with a ketal or acetal of formula III in the presence of an acid catalyst system containing at least one strong acid while maintaining, in the reaction mixture, a substantial excess of the ketal or acetal as compared with the tertiary allyl alcohol.

In carrying out this aspect of the process of this invention, the ratio of the ketal or acetal of formula III to the tertiary allyl alcohol of formula II in the reaction mixture is from about 3 to about 100 moles of the ketal or acetal per mole of the tertiary allyl alcohol. Preferably, the molar ratio of the ketal or acetal and the tertiary allyl alcohol is maintained at from about 50:1 to about 20:1 in the reaction mixture, particularly at about 30:1. Maintaining a substantial excess of the ketal or acetal of formula III in the reaction mixture promotes the formation of an azeotrope consisting essentially of the ketal or acetal of formula III and the alcohol of formula IV which is formed as the by-product of the main reaction. The azeotrope formed from the alcohol of formula IV can be easily removed from the reaction mixture by conventional reactive distillation techniques, as the production of $\gamma,\delta$-unsaturated carbonyl compound of formula I proceeds.

In carrying out the invention in a batch-wise fashion, it is particularly preferred to utilize between about 10 and 50 moles of the ketal or acetal, particularly about 40 moles, per mole of the tertiary allyl alcohol in the reaction mixture at the beginning of the reaction. Then, in accordance with the particularly preferred batchwise procedure, additional tertiary allyl alcohol of formula II and ketal or acetal of formula III are incrementally added to the reaction mixture as the main reaction proceeds. Generally the reaction of this invention is carried out utilizing at least 3 incremental additions of the compound of formula II to the reaction medium, preferably from about 3 to 30 increments.

In this reaction the acetal or ketal of formula III can be added in an amount in excess of the amount required to react with the tertiary allyl alcohol of formula II. In carrying out the incremental addition of the tertiary allyl alcohol, the amounts of this reactant are not critical. It is also preferred to incrementally add the ketal or acetal of formula III so that an excess thereof is maintained in the reaction mixture sufficient to remove the alcohol of formula IV as an azeotrope, as the alcohol continues to be evolved in the reaction mixture. Preferably, the molar ratio of the ketal or acetal of formula III to the tertiary allyl alcohol of formula II being incrementally added to the reaction mixture is from about 2:1 to 1:1 with a ratio of about 1.5:1 being particularly preferred.

If desired, the foregoing, particularly preferred, batch-wise procedure can be modified for continuous operation. This can be done in accordance with conventional, reactive distillation techniques.

In carrying out the second embodiment of this invention, the reaction mixture should contain at least about 0.01 to 0.5 wt. percent, preferably about 0.2 wt. percent, of a strong acid. If desired, the reaction mixture can also contain a weak acid, to form the acid catalyst system described above as the first embodiment of this invention. In accordance with the second embodiment of this invention, it is preferred that the reaction mixture contain an acid catalyst system initially comprising about 0.001 to 0.2 moles of a weak acid and about 0.0005 to 0.010 moles of a strong acid per 0.07 moles of the tertiary allyl alcohol of formula II utilized in the reaction mixture at the beginning of the reaction. As additional tertiary allyl alcohol of formula II and ketal or acetal of formula III are added incrementally to the reaction mixture, further additions of acid to the reaction mixture can be made, if desired. Preferably, no further amount of acid is added to the reaction mixture, and the size of the reaction mixture is kept approximately constant by, for example, removing the azeotrope of the alcohol of formula IV and the ketal or acetal of formula III, by distillation, as the main reaction proceeds.

By the process of this invention, employing the catalyst system consisting of a strong acid and a weak acid, 80 percent yields of the $\gamma,\delta$-unsaturated carbonyl compound of formula I can be realized utilizing reaction times on the order of about 15 hours. In addition, by continuously maintaining a substantial excess of the ketal or acetal of formula III in the reaction mixture, the 80% yields of $\gamma,\delta$-unsaturated carbonyl compound can be realized with nearly complete consumption of the tertiary allyl alcohol of formula II, without the need for excessive reaction periods and without the need for utilizing excessively large amounts of the ketal or acetal of formula III.

The $\gamma,\delta$-unsaturated carbonyl compound of formula I can be isolated in pure form in a conventional manner from the mixture resulting from reacting the tertiary allyl alcohol of formula II with the ketal or acetal of formula III in the presence of the acid catalyst system of this invention. For example, the $\gamma,\delta$-unsaturated carbonyl compound can be conveniently isolated by one or more fractional distillation steps, carried out until the product is of the desired purity.

The $\gamma,\delta$-unsaturated carbonyl compounds of formula I obtained in accordance with this invention can be used as odorants for perfume purposes. The compounds of formula I can also be used as intermediates for the manufacture of other chemical compounds, such as for example, substituted ionones, vitamin A, E and $K_1$ or carotenoids.

The example which follows further illustrates the process of this invention.

EXAMPLE 1

Into a 1 liter stainless steel cylinder were placed 12.5 g. of 3-methyl-1-buten-3-ol, 300 g. of acetone dimethyl ketal (2,2-dimethoxypropane) and 6.9 ml. of an acid catalyst system consisting of 8 g. of $H_3PO_4$ (85% by wt.) and 100 ml. of glacial acetic acid. The total weight of the contents was adjusted to 600 g. with ca. 280 g. of acetone dimethyl ketal. The tightly closed cylinder was immersed in a stirred, preheated oil bath at 150°C. for 1 hour. After 1 hour, the cylinder was cooled in a ice bath and the contents were transferred to a 1 liter round bottomed flask without rinsing. The reaction mixture was subjected to distillation through a 68 cm Goodloe packed column at atmospheric pressure until the head temperature reached 64°C., most of the acetone dimethyl ketal-methanol azeotrope distilling at about 58°C. The distillate weighed around 30 g. and contained acetone dimethyl ketal, methanol, acetone, iospropenyl isopropenyl ether, and traces of isoprene. At this point, the distillation was stopped. To the cooled residual pot solution was added 12.5 g. of 3-methyl-1-buten-3-ol and the total weight was again adjusted to 600 g. with about 20 to 30 g. of fresh acetone dimethyl ketal. This slightly yellow reaction mixture was transferred to the steel cylinder which was again heated for 1 hour at 150°C. The distillation process to 64°C., the addition of 12.5 g. of fresh 3-methyl-1-buten-3-ol and about 20 to 30 grams of fresh acetone dimethyl ketal, and the heating to 150°C. for 1 hour were repeated ten more times, until a total of 150 g. of 3-methyl-1-buten-3-ol had been utilized. After the last addition of 3-methyl-1-buten-3-ol, the 1 hour heating periods were repeated four more times with replacement of the distillate with acetone dimethyl ketal only. After a total of 16 one-hour heating periods, the reaction was almost complete. The isolation of 6-methyl-5-hepten-2-one was carried out by distilling the final reaction mixture, first at atmospheric pressure using the same Goodloe column ($T_{dist.}$ 38–74°), followed by vacuum distillation of the residue through a 10 cm Vigreux column. The vacuum distillation yielded a forerun (22°–55°/12 mm.) of 118.3 g. containing methylheptenone, a main fraction of 157.0 g. (56°–62°/12 mm.), consisting essentially of methylheptenone, and a residue of 7.5 g. The forerun was redistilled at atmospheric pressure to give 14.6 g. of methylheptenone; B.P. 160°–164°. Thus, 150 g. of 3-methyl-1-buten-3-ol yielded a total of 171.6 g. (78%) of methylheptenone of 97% purity.

I claim:

1. In a process for obtaining γ,δ-unsaturated carbonyl compounds of the formula:

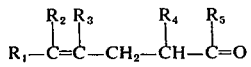

wherein $R_1$ is selected from the group consisting of (a) a saturated hydrocarbon group, (b) an unsaturated hydrocarbon group, (c) an aralkyl group, (d) an aryl group, and (e) an oxygen-containing derivative of (a), (b), and (c) wherein the oxygen is in the form of free hydroxy, esterified hydroxy, wherein the esterifying group is an acyloxy group in which the acyl moiety is from an acid selected from the group consisting of lower alkanoic acids and benzoic acid, and etherified hydroxy selected from the group consisting of lower alkoxy and phenyloxy, and wherein the oxygen atom is attached to an aliphatic carbon atom on said group; $R_2$ is a lower aliphatic hydrocarbon; $R_3$, $R_4$ and $R_5$ are selected from the group consisting of hydrogen and a lower aliphatic hydrocarbon and wherein $R_1$ taken together with $R_2$ can form a carbocyclic ring, and $R_4$ taken together with $R_5$ can form a carbocyclic ring;

comprising the steps of reacting a tertiary allyl alcohol of the formula:

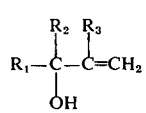

wherein $R_1$, $R_2$ and $R_3$ are as above;
with an acetal or ketal of the formula:

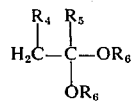

wherein $R_4$ and $R_5$ are as above and $R_6$ is alkyl; in the presence of a strong acid having a pK value of 0.4 to 3, the improvement which comprises forming a catalyst system by adding to said strong acid a weak acid having a pK value of from 4.5 to 10 and selected from the group consisting of lower alkanoic acids, dinitrobenzoic acids and dinitrophenol; forming a reaction mixture consisting essentially of said acetal or ketal and said acid catalyst system, said acid catalyst system being present in an amount of from 0.1% to 10% by weight based upon the weight of the reaction mixture with the acid catalyst containing from 2 to 15% by weight of the strong acid and from 85 to 98% by weight of the weak acid, to provide 3 to 100 moles of said acetal per mole of said tertiary allyl alcohol; incrementally adding said tertiary allyl alcohol to said reaction mixture by a. reacting the first increment of the tertiary allyl alcohol with the reaction mixture at a temperature of from 50°C. to 200°C. and a pressure of from 10 to 50 atmospheres to form said carbonyl compound and a primary alcohol of the formula

wherein $R_6$ is as above
said alcohol forming an azeotrope with said acetal or ketal;

b. distilling off said azeotrope from said reaction mixture; and c. adding subsequent increments of said tertiary alcohol to said reaction mixture, with each of said subsequent increments being added after said reaction of the previous increment with said reaction mixture and said distillation of said azeotrope formed has been carried out.

2. The process of claim 1 wherein said weak acid is acetic acid.

3. The process of claim 1 wherein the acetal 2,2-dimethoxy propane and the tertiary allyl alcohol 3- methyl-1-buten-3-ol is reacted to form the carbonyl compound 6-methylhepten-2-one.

4. The process of claim 3 wherein said weak acid is acetic acid.

* * * * *